(12) United States Patent
Ikuta

(10) Patent No.: US 9,427,860 B2
(45) Date of Patent: Aug. 30, 2016

(54) POWER TOOL

(71) Applicant: MAKITA CORPORATION, Anjo-shi, Aichi (JP)

(72) Inventor: Hiroki Ikuta, Anjo (JP)

(73) Assignee: MAKITA CORPORATION, Anjo-Shi (JP)

( * ) Notice: Subject to any disclaimer, the term of this patent is extended or adjusted under 35 U.S.C. 154(b) by 570 days.

(21) Appl. No.: 13/768,653

(22) Filed: Feb. 15, 2013

(65) Prior Publication Data

US 2013/0213684 A1    Aug. 22, 2013

(30) Foreign Application Priority Data

Feb. 21, 2012    (JP) ................. 2012-035665

(51) Int. Cl.
| | | |
|---|---|---|
| *B25F 5/00* | (2006.01) | |
| *A61B 17/14* | (2006.01) | |
| *B24B 23/04* | (2006.01) | |
| *B27B 19/00* | (2006.01) | |

(52) U.S. Cl.
CPC ............ *B25F 5/001* (2013.01); *A61B 17/14* (2013.01); *B24B 23/04* (2013.01); *B27B 19/006* (2013.01)

(58) Field of Classification Search
USPC ................................. 493/90, 213
See application file for complete search history.

(56) References Cited

U.S. PATENT DOCUMENTS

| | | | | |
|---|---|---|---|---|
| 2,588,216 A * | 3/1952 | De Graaf | ............... | E05D 11/02 16/274 |
| 3,452,226 A * | 6/1969 | Hettich | ............... | B23B 45/001 173/117 |
| 3,505,733 A * | 4/1970 | Holden | ............... | A61B 17/14 30/166.3 |
| 4,858,700 A * | 8/1989 | Shafer | ............... | E21B 7/025 173/185 |
| 5,533,925 A | 7/1996 | Sato | | |
| 5,768,933 A * | 6/1998 | Tanner | ............... | B27B 19/006 30/218 |
| 8,109,809 B2 * | 2/2012 | Bohne | ............... | B27B 19/006 451/344 |
| 2001/0046335 A1 * | 11/2001 | Keller | ............... | F16H 57/0497 384/13 |
| 2003/0220058 A1 | 11/2003 | Pollak et al. | | |
| 2004/0007426 A1 * | 1/2004 | Keller | ............... | F16H 57/0497 184/5 |
| 2004/0069513 A1 * | 4/2004 | Wolf | ............... | B24B 23/022 173/216 |
| 2009/0114398 A1 * | 5/2009 | Buytaert | ............... | E21B 33/1291 166/380 |
| 2009/0311952 A1 * | 12/2009 | Zaiser | ............... | B24B 23/04 451/357 |
| 2011/0017483 A1 * | 1/2011 | Baumann | ............... | B25D 11/062 173/162.2 |

(Continued)

FOREIGN PATENT DOCUMENTS

| | | |
|---|---|---|
| DE | 4403538 A1 | 8/1994 |
| DE | 102007018466 A1 | 10/2008 |

(Continued)

OTHER PUBLICATIONS

Oct. 9, 2015 Search Report issued in European Patent Application No. 13155769.6.

*Primary Examiner* — Hemant M Desai
*Assistant Examiner* — Mobeen Ahmed
(74) *Attorney, Agent, or Firm* — Oliff PLC

(57) ABSTRACT

An electric oscillating tool which actuates a tool around a spindle is provided. The electric oscillating tool comprises a motor, the spindle which is driven by the motor, and a driving transmission member which transmits a rotational output of the motor to the spindle. The driving transmission member includes an eccentric moving member, a driven arm, a spindle connecting arm, and a pin which connects the driven arm and the spindle connecting arm in a relatively rotatable manner. The eccentric moving member comprises an eccentric shaft which moves eccentrically around a rotational shaft of the motor, a first bearing, and a second bearing.

5 Claims, 4 Drawing Sheets

(56) References Cited

U.S. PATENT DOCUMENTS

| | | | | |
|---|---|---|---|---|
| 2011/0036609 A1* | 2/2011 | Blickle | ............... | B24B 23/028 173/213 |
| 2011/0048753 A1* | 3/2011 | Zaiser | ................... | B23D 51/16 173/213 |
| 2011/0209888 A1* | 9/2011 | Elsworthy | .......... | B23B 31/1071 173/217 |
| 2011/0260414 A1* | 10/2011 | Ota | ........................ | B24B 23/02 279/8 |
| 2013/0181414 A1* | 7/2013 | Haman | ............... | B27B 19/006 279/144 |
| 2014/0020918 A1* | 1/2014 | Klabunde | ............. | B23D 47/12 173/49 |
| 2014/0130301 A1* | 5/2014 | Shargh | ................... | E05D 11/02 16/274 |
| 2015/0034353 A1* | 2/2015 | Huo | ...................... | H02K 7/075 173/217 |

FOREIGN PATENT DOCUMENTS

| | | |
|---|---|---|
| DE | 102008004638 A1 | 7/2009 |
| JP | A 2011-230204 | 11/2011 |
| WO | 94/04312 A1 | 3/1994 |

* cited by examiner

POWER TOOL

CROSS REFERENCE TO RELATED APPLICATION

The present application claims priority from Japanese Patent Applications No. 2012-035665 filed on Feb. 21, 2012, the disclosure of which is incorporated herein by reference in its entirety.

FIELD OF THE INVENTION

The invention relates to a power tool which actuate a clamped tool.

BACKGROUND OF THE INVENTION

Japanese Unexamined Patent Application Publication No. 2011-230204 discloses a power tool which actuates a tool clamped and fixed to a driving shaft. In this power tool, a fork-shaped engaging portion of a swinging arm which is attached to the driving shaft engages with an outer surface of a bearing which is attached on an eccentric shaft disposed at an end of a motor shaft. When the engaging portion moves and rotates together with the eccentric shaft around the motor shaft, the swinging arm rotationally reciprocates around the driving shaft as the center of a rotation. Therefore, the driving shaft rotationally reciprocates and swings the tool around the driving shaft.

SUMMARY OF THE INVENTION

Problem to be Solved by the Invention

As to such construction in which the fork-shaped engaging portion is reciprocated via the bearing, in case that a cylindrical bearing is utilized as the bearing, the specific part of the engaging portion is always contacted with a corner portion of the bearing, and thereby an abrasion of the engaging portion and the bearing is occurred considerably. Accordingly, the power tool disclosed in Japanese Unexamined Patent Application Publication No. 2011-230204 comprises a bearing which is formed with a curved outer surface in a cross-section on a plane which is parallel to a direction in which the swinging arm is reciprocated. Therefore, a contact point of the engaging portion and the bearing is changed according to an angular position of the swinging arm, and thereby an abrasion of the engaging portion and the bearing is regulated. However, since the outer surface of the bearing is formed as a curved surface, such bearing is relatively expensive than a cylindrically shaped bearing. In this respect, there is still room for improvement.

An object of the invention is, in consideration of the above described problem, to provide an improved technique with respect to a driving of a tool of a power tool.

Means for Solving the Problem

Above-mentioned object is achieved by the claimed invention. According to a preferable aspect of the invention, a power tool which actuates a tool around a predetermined axis is provided. The power tool comprises a motor, a driving shaft which is driven by the motor, and a driving transmission member which transmits a rotational output of the motor to the driving shaft. The driving transmission member includes an eccentric shaft which moves eccentrically around a rotational shaft of the motor, a first member to which a movement of the eccentric moving member is transmitted, a second member which is connected to the driving shaft, and a pivot portion which connects the first member and the second member in a relatively rotatable manner.

According to the invention, the power tool has the pivot portion which connects the first member with the second member in a relatively rotatable manner, therefore the first member moves approximately parallel against the eccentric moving member in a rotational axis of the motor. Accordingly, it is not necessary to form the outer surface of the eccentric moving member into a curve in a cross section which is parallel to the rotational axis of the motor. Namely a ready-made cylindrical bearing is utilized as the eccentric moving member, therefore a cost of the power tool is reduced.

According to a further preferable aspect, the eccentric moving member includes an eccentric portion which is arranged to be offset to the center of the rotational shaft, and two bearings which are arranged on a periphery of the eccentric portion. The first member includes two arms which face to each other and contact with respective peripheries of the two bearings. Further, said two bearings are arranged in line in an axial direction of the rotational shaft.

When the first member inclines, said two arms contact with corner parts of the bearings respectively, the corner parts being opposite to each other. Accordingly, in case that only one bearing is provided to the power tool, because a slide between the bearing and the arm is occurred, an abrasion of the bearing and the arm is increased. However, according to this aspect, because two bearings are provided, when the first member inclines, one arm contacts with a corner part of one bearing and the other arm contacts with a corner part of the other bearing. Therefore, while a motion of the eccentric moving member is transmitted to the first member, said two bearings are moved in opposite direction to each other respectively. Namely, a slide is not occurred between the bearings and the arm, therefore each lifetime of the bearings and the arm is improved.

According to a further preferable aspect, the pivot portion and the eccentric moving member are arranged to be equally distant from the driving shaft in the axial direction of the rotational shaft.

According to this aspect, a length of the first member in an axial direction of the rotational shaft of the motor is shortened. Therefore, a size of the power tool is to be relatively small.

According to a further preferable aspect, a tool attached shaft to which the tool is attached is arranged coaxially to the driving shaft. The feature of "the tool attached shaft is arranged coaxially to the driving shaft" preferably includes a feature in which the tool attached shaft is provided as other member from the driving shaft, the tool attached shaft and the driving shaft being arranged coaxially to each other, and a feature in which the driving shaft and the tool attached shaft are integrally formed and the tool is attached to the driving shaft.

In case that the tool attached shaft and the driving shaft are parallelly and separately arranged to each other, a size of the power tool in a direction in which the tool attached shaft is apart from the driving shaft is enlarged. However, according to this aspect, because the tool attached shaft and the driving shaft are arranged coaxially, in comparison with a construction in which the tool attached shaft and the driving shaft are not arranged coaxially, a size of the power tool is to be relatively small. Further, in case that the tool attached shaft and the driving shaft are parallelly and separately arranged to each other, a transmitting member which transmits a driving of the driving shaft to the tool attached shaft to actuate and rotate the tool attached shaft around a predetermined direction is needed. Therefore, a number of components of the power tool is increased. However, according to this aspect, in case that the tool attached shaft and the driving shaft are integrally provided with each other, a number of components of the power tool is reduced.

According to a further preferable aspect, the pivot portion includes a lubricant holding portion which holds lubricant for lubricating the first member and the second member being rotating.

Generally, a lubricant is provided for a rotatable member to move a rotatable member smoothly. According to this aspect, because the pivot portion includes the lubricant holding portion, the first member and the second member are rotated smoothly. Further, because the lubricant is held in the lubricant holding member, the lubricant is prevented from flying apart from the driving transmission member.

According to a further preferable aspect, the pivot portion includes an elongate member which is arranged parallel to the driving shaft. The elongate member preferably includes a feature in which the elongate member is formed integrally with one of the first member and the second member, and a feature in which the elongate member is provided separately from the first member and the second member.

According to this aspect, the first member and the second member are connected to each other via the elongate member which is arranged parallel to the driving shaft, therefore the first member is parallelly moved against the eccentric moving member in a rotational axial direction of the motor. Further, the second member is rotated reciprocatingly around the driving shaft.

Accordingly, an improved technique with respect to a driving of the tool of the power tool is provided.

Other objects, features and advantages of the invention will be readily understood after reading the following detailed description together with the accompanying drawings and the claims.

DESCRIPTION OF THE PREFERRED
EMBODIMENTS

Each of the additional features and method steps disclosed above and below may be utilized separately or in conjunction with other features and method steps to provide and manufacture improved power tools and method for using such the power tools and devices utilized therein. Representative examples of the invention, which examples utilized many of these additional features and method steps in conjunction, will now be described in detail with reference to the drawings. This detailed description is merely intended to teach a person skilled in the art further details for practicing preferred aspects of the present teachings and is not intended to limit the scope of the invention. Only the claims define the scope of the claimed invention. Therefore, combinations of features and steps disclosed within the following detailed description may not be necessary to practice the invention in the broadest sense, and are instead taught merely to particularly describe some representative examples of the invention, which detailed description will now be given with reference to the accompanying drawings.

First Embodiment

A first embodiment will be explained with reference to FIG. 1 to FIG. 3. The first embodiment is one example of the invention to be applied to an electric oscillating tool as a power tool.

Figure 1:
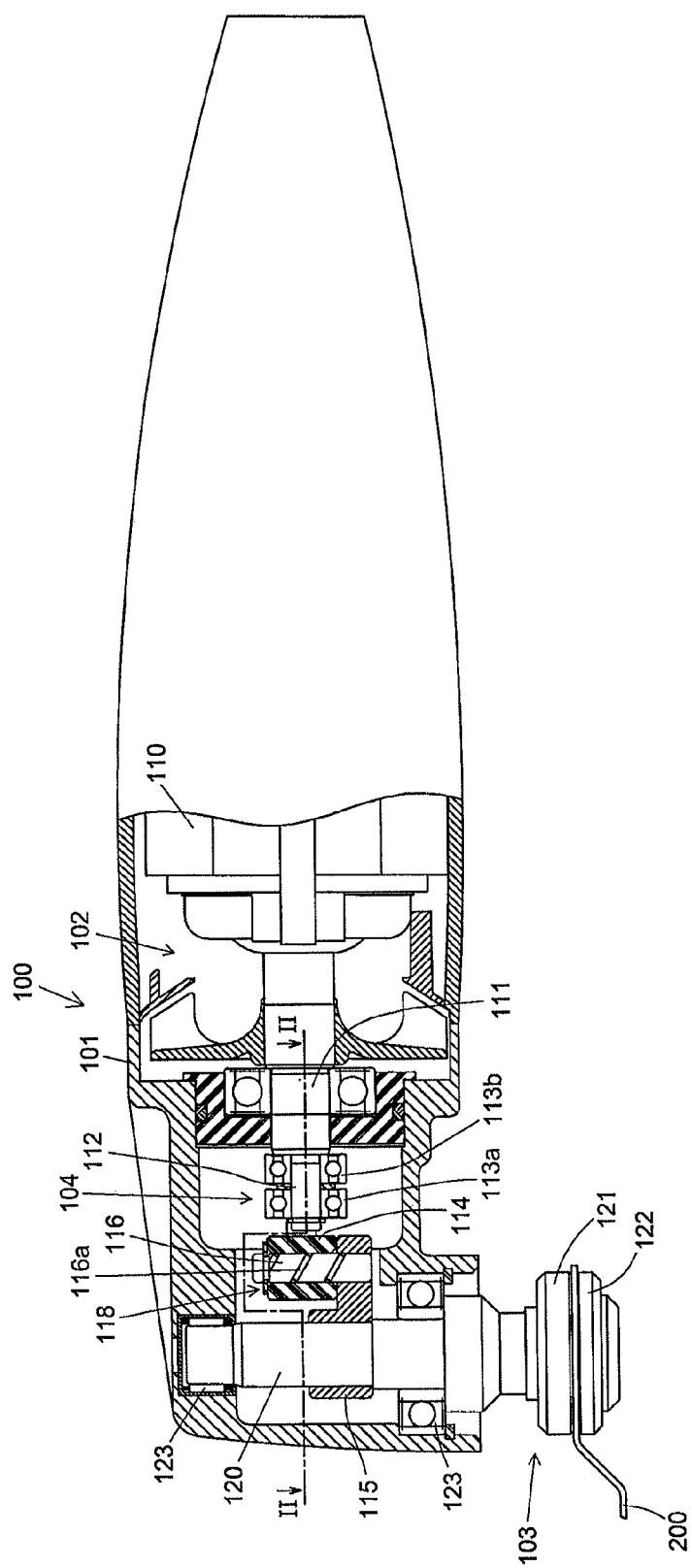
FIG. 1 shows a partial cross-sectional view of an electric oscillating tool according to a first embodiment.

As shown in FIG. 1, the electric oscillating tool 100 is one of the power tools to which a plurality kind of tools like a blade, a sanding pad and so on are selectively attached, and the oscillating tool 100 oscillates the attached tool and thereby the oscillating tool 100 performs a predetermined operation based on the attached tool. In the first embodiment, a blade 200 is utilized to explain as one example of the tool. Further, the blade 200 and so on is one example corresponding to "a tool" of the invention.

Figure 2:
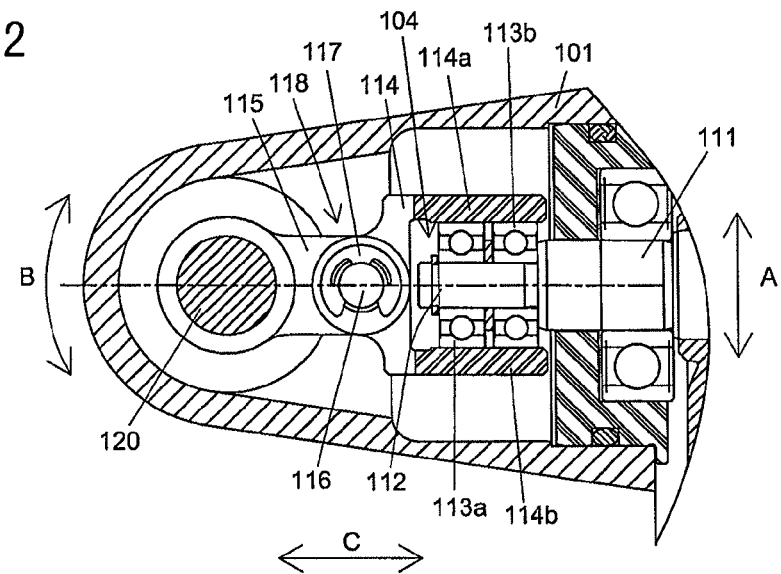
FIG. 2 show a cross-sectional view taken from line II-II of FIG. 1.
Figure 3:
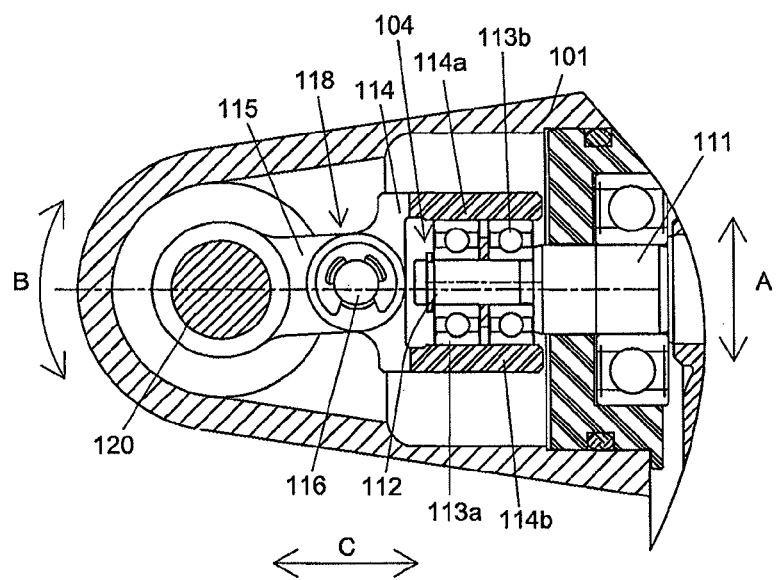
FIG. 3 shows a cross-sectional view in which an eccentric shaft is moved to upper side of FIG. 3 in comparison with FIG. 2.

As shown in FIG. 1 and FIG. 2, the electric oscillating tool 100 is mainly provided with a main housing 101, and a driving mechanism 102 and a tool holding mechanism 103 which are housed by the main housing 101.

The driving mechanism 102 is mainly provided with a motor 110, an eccentric moving portion 104, a driven arm 114, a spindle connecting arm 115, and a pin 116. The eccentric moving portion 104 is mainly provided with an eccentric shaft 112, a first bearing 113a and a second bearing 113b. The eccentric shaft 112 is provided at an end of an output shaft 111 of the motor 110 to be offset from a rotational axis of the output shaft 111 and is extended parallel to the rotational axis. The first bearing 113a and the second bearing 113b are arranged and attached on a periphery of the eccentric shaft 112. The first bearing 113a and the second bearing 113b are provided side by side to each other along a direction in which the eccentric shaft 112 extends, namely along the rotational axis of the output shaft 111. The eccentric moving portion 104 is one example corresponding to "an eccentric moving member" of the invention. Further, the eccentric shaft 112 is one example corresponding to "an eccentric portion" of the invention. Further, the first bearing 113a and the second bearing 113b are one example corresponding to "two bearings" of the invention.

As shown in FIG. 2, the driven arm 114 includes a first arm 114a and a second arm 114b which respectively extend toward the motor 110 side from the spindle connecting arm 115 side. The first arm 114a and the second arm 114b are respectively disposed at two points which oppose to each other at an outer region of the first bearing 113a and the second bearing 113b such that the first arm 114a and the second arm 114b are contactable with each of the first bearing 113a and the second bearing 113b. Namely, the driven arm 114 is disposed within a moving area of the first bearing 113a and the second bearing 113b, where the first bearing 113a and the second bearing 113b are moved. The driven arm 114 is one example corresponding to "a first member" of the invention. Further, the first arm 114a and the second arm 114b are one example corresponding to "two arms" on the invention.

As shown in FIG. 1 and FIG. 2, the spindle connecting arm 115 is connected to a spindle 120 such that the spindle connecting arm 115 is rotated integrally with the spindle 120. One side of the spindle connecting arm 115, which is opposite to another side connected to the spindle 120, is connected to the driven arm 114 via the pin 116. In particular, a through-hole into which the pin 116 is inserted is formed at both of the driven arm 114 and the spindle connecting arm 115. The pin 116 is inserted into the through-hole and engaged with a C-ring 117 at one end of the pin 116, and thereby the pin 116 is connected to the driven arm 114. Accordingly, the driven arm 114 and the spindle connecting arm 115 are connected to each other in a relatively rotatable manner. The pin 116 and through-holes of the driven arm 114 and the spindle connecting arm 115 form a pivot 118. The spindle connecting arm 115 is one example corresponding to "a second member" of the invention. Further, the pivot 118 is one example corresponding to "a pivot portion", and the pin 116 is one example corresponding to "an elongate member" of the invention.

As shown in FIG. 1, the pin 116 is arranged parallel to the spindle 120. A spiral groove 116a is formed on an outer surface of the pin 116. Further, lubricant is provided between the driven arm 114 and the pin 116 as well as the spindle connecting arm 115 and the pin 116, for a smooth rotation of the driven arm 114 and the spindle connecting arm 115 to each other. The groove 116a is one example corresponding to "a lubricant holding portion" of the invention.

The tool holding mechanism 103 is a mechanism which holds the blade 200 and oscillates the blade 200 by transmitting an output of the motor 110 to the blade 200. The tool holding mechanism 103 is mainly provided with the spindle 120, an inner flange 121 and an outer flange 122.

The spindle 120 is formed as an elongate member and disposed such that a longitudinal direction of the spindle 120 crosses the output shaft 111 of the motor 110. The spindle 120 is supported at two parts in the longitudinal direction by the main housing 101 via two bearings 123 such that the spindle 120 is rotatable around the longitudinal direction. The inner flange 121 and the outer flange 122 are attached at a distal end of the spindle 120, which is disposed at an outer region of the main housing 101. The outer flange 122 is detachable to the spindle 120. Accordingly, the blade 200 is clamped between the inner flange 121 and the outer flange 122. The spindle 120 is one example corresponding to "a driving shaft", "a tool attached shaft" respectively.

As to the electric oscillating tool 100 described above, as shown in FIG. 2, when the motor is driven, a rotational motion of the output shaft 111 is changed into a reciprocating motion in a direction indicated by an arrow A (hereinafter referred to as an A-direction) by the eccentric shaft 112, the first bearing 113a and the second bearing 113b. As shown in FIG. 3, when the eccentric shaft 112 is moved upward in FIG. 3, the driven arm 114 is moved to be close to the spindle 120 as well as upward in FIG. 3 by contacting the first bearing 113a and the second bearing 113b with the first arm 114a. At this time, the spindle connecting arm 115 which is connected to the driven arm 114 via the pin 116 is rotated around the spindle 120. Namely, the reciprocating motion of the eccentric shaft 112 in the A-direction is changed into a rotational motion in a circumference direction (hereinafter referred to as a B-direction) of the spindle 120, the rotational motion defined within a predetermined angular region. Therefore, the blade 200 clamped by the inner flange 121 and the outer flange 122 is oscillated, and thereby the predetermined operation to a workpiece is accomplished.

According to the first embodiment described above, because the driven shaft 114 and the spindle connecting arm 115 are connected via the pin 116 in a relatively rotatable manner, the driven arm 114 is moved substantially parallel to a direction (a C-direction in FIG. 2) which extends along a line toward the spindle 120 from the eccentric moving portion 104 which is provided with the eccentric shaft 112, the first bearing 113a and the second bearing 113b. Namely, because the driven arm 114 does not incline against the first bearing 113a and the second bearing 113b when the driven arm 114 moves, each outer surface of the first bearing 113a and the second bearing 113b is not necessary to form into a curved manner in a cross-section which is parallel to the C-direction. Therefore, a ready-made cylindrically shaped bearing is utilized as the first bearing 113a and the second bearing 113b respectively. Accordingly, a cost reduction of the electric oscillating tool 100 is achieved.

Unlike the first embodiment, in case that the driven arm and the spindle connecting arm are connected in a fixed manner, while the electric oscillating tool is driving, the driven arm is rotated together with the spindle connecting arm. As a result, a prying force is exerted on the bearing which is contacted with the driven arm. Namely, the driven arm exerts a large moment on the bearing. However, according to the first embodiment, because the driven arm 114 and the spindle connecting arm 115 are connected in a relatively rotatable manner via the pin 116, while the electric oscillating tool 100 is actuating, the driven arm 114 does not rotate integrally with the spindle connecting arm 115. Therefore, the prying force on which the driven arm 114 applies the first bearing 113a and the second bearing 113b is regulated. Namely, a moment which is exerted on the first bearing 113a and the second bearing 113b by the driven arm 114 is reduced. Therefore, respective lifetime of the first bearing 113a and the second bearing 113b is improved.

Further, unlike the first embodiment, in case that the driven arm and the spindle connecting arm are fixedly connected to each other, because the driven arm is rotated integrally with the spindle connecting arm, a displacement of the driven arm in the C-direction in FIG. 2 is increased. However, according to the first embodiment, because the driven arm 114 and the spindle connecting arm 115 are connected to each other in a relatively rotatable manner, a displacement of the driven arm in the C-direction in FIG. 2 is decreased. Namely, a slide amount between the driven arm 114 and the first bearing 113a, the second bearing 113b is reduced. As a result, an abrasion of each component of the driven arm 114, the first bearing 113a and the second bearing 113b is regulated.

Further, according to the first embodiment, the driven arm 114 is moved substantially parallel to the C-direction while the driven arm 114 is reciprocated in the A-direction. Therefore, a ready-made cylindrical bearing is utilized as the first bearing 113a and the second bearing 113b respectively. Accordingly, a special-formed bearing is not necessary for the electric oscillating tool 100, and thereby a cost of the electric oscillating tool 100 is reduced.

Further, according to the first embodiment, in case that the driven arm 114 is inclined against the first bearing 113a and the second bearing 113b, the first arm 114a contacts with one bearing among the first bearing 113a and the second arm 114, and further the second arm 114b contacts with another bearing among the first bearing 113a and the second bearing 113b. Accordingly, the first bearing 113a and the second bearing 113b rotate respectively in opposite directions to each other around the eccentric shaft 112.

Unlike the first embodiment, in case that only one bearing is provided on the eccentric shaft 112 and the driven arm 114 is inclined against said only one bearing, both of the first arm 114a and the second arm 114b are contact with said only one bearing. Therefore, the first arm 114a and the second arm 114b slide on the bearing. However, according to the first embodiment, in case that the driven arm 114 is inclined against the first bearing 113a and the second bearing 113b, the first bearing 113a and the second bearing 113b rotate respectively in opposite directions to each other around the eccentric shaft 112. Accordingly, a slide between the first arm 114a, the second arm 114b and the first bearing 113a, the second bearing 113b is regulated. Namely, an abrasion of the driven arm 114, the first bearing 113a and the second bearing 113b is regulated.

Further, according to the first embodiment, the spiral groove 116a is formed on the outer surface of the pin 116. Therefore, the lubricant provided between the driven arm 114, the spindle connecting arm 115 and the pin 116 is held by the spiral groove 116a. Accordingly, the lubricant is prevented from flying apart within the main housing 101. Further, because the groove 116a is formed as spiral, the lubricant is moved on the outer surface of the pin 116 along the groove 116a. As a result, the driven arm 114 and the spindle connecting arm 115 are relatively rotated smoothly.

Second Embodiment

A second embodiment will be explained with reference to FIG. 4 to FIG. 6. In the second embodiment, the driven arm, the spindle connecting arm and the bearing are different from the first embodiment. Other components are similar to the first embodiment. Therefore such other components will be signed same reference number as the first embodiment and omitted to explain for convenience.

Figure 4:
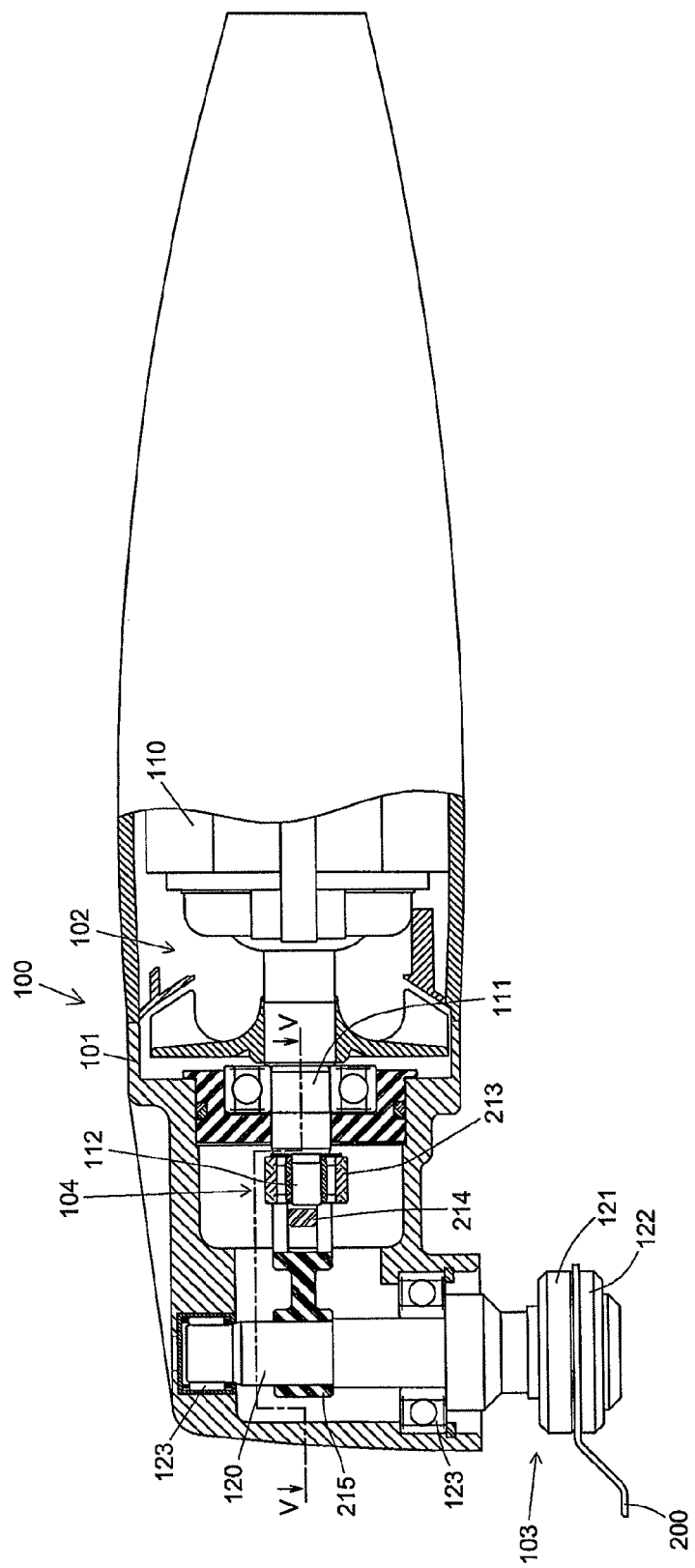
FIG. 4 shows a partial cross-sectional view of an electric oscillating tool according to a second embodiment.

As shown in FIG. 4, in the second embodiment, only one bearing 213 is provided on the eccentric shaft 112. Further, as shown in FIG. 5 and FIG. 6, a driven arm 214 includes a first arm 214a and a second arm 214b which are disposed at an outer region of a bearing 213 to be contactable with the bearing 213. Further, a connecting part of the driven arm 215 and a spindle connecting arm 215 is parallelly arranged with the eccentric moving portion 104 which is formed by the eccentric shaft 112 and the bearing 213 in a direction (a C-direction in FIG. 5) which extends along a line toward the spindle 120 from the eccentric moving portion 104. Namely, a distance between the spindle 120 and the eccentric moving portion 104 and a distance between the spindle 120 and the pin 116 are defined as the same distance.

In the second embodiment, when the motor 110 is driven, a rotational motion of the output shaft 111 is changed into a reciprocating motion in a direction indicated by an arrow A (hereinafter referred to as an A-direction) by the eccentric shaft 112 and the bearing 213. At this time, the bearing 213 contacts with the first arm 214a or the second arm 214b and moves the driven arm 214. Due to a movement of the driven arm 214, the spindle connecting arm 215 which is connected to the driven arm 214 via the pin 116 is rotated around the spindle 120. Namely, the reciprocating motion of the eccentric shaft 112 in the A-direction is changed into a rotational motion in a circumference direction (hereinafter referred to as a B-direction) of the spindle 120, the rotational motion defined within a predetermined angular region. Therefore, the blade 200 clamped by the inner flange 121 and the outer flange 122 is oscillated, and thereby the predetermined operation to a workpiece is accomplished.

Figure 5:
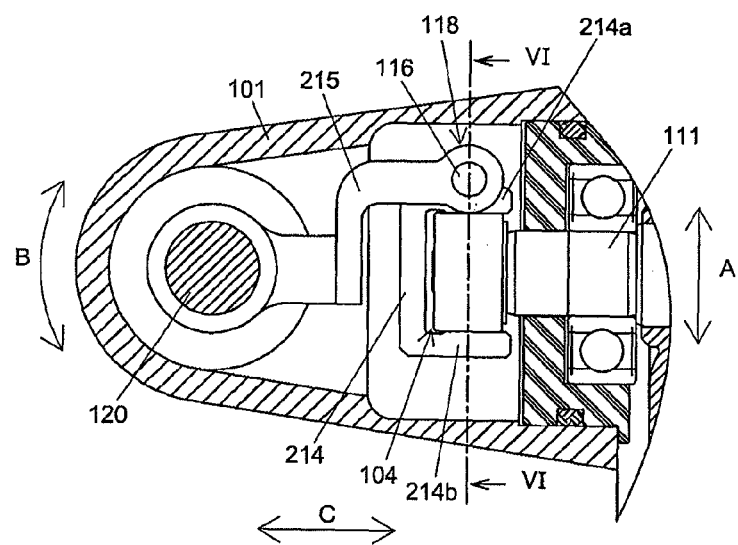
FIG. 5 shows a cross-sectional view taken from line V-V of FIG. 4.
Figure 6:
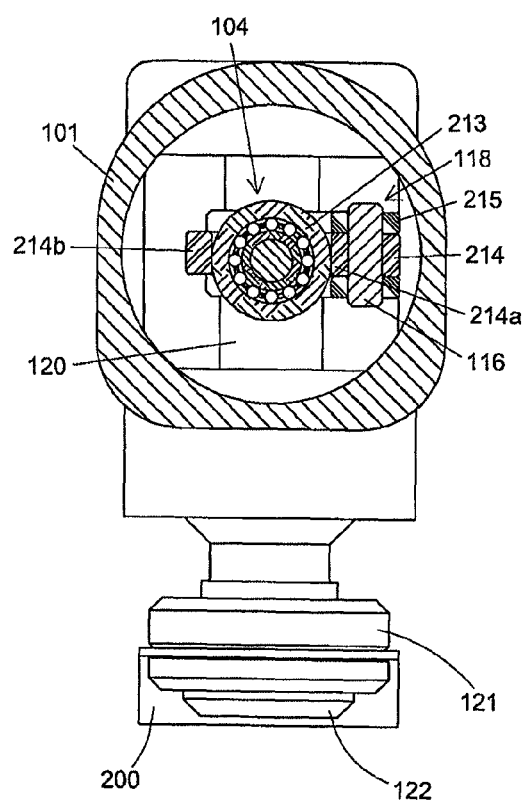
FIG. 6 shows a cross-sectional view taken from line VI-VI of FIG. 5.

According to the second embodiment described above, being similar to the first embodiment, because the driven arm 214 and the spindle connecting arm 215 are connected via the pin 116 in a relatively rotatable manner, the driven arm 214 is moved substantially parallel to the C-direction in FIG. 5. Namely, because the driven arm 214 does not incline against the bearing 213, an outer surface of the bearing 213 is not necessary to be curved in a cross-section which is parallel to the C-direction. Therefore, a ready-made cylindrically shaped bearing is utilized as the bearing 213. Accordingly, a cost reduction of the electric oscillating tool 100 is achieved.

Further, according to the second embodiment, the distance from the spindle 120 to the eccentric moving portion 104 and the distance from the spindle 120 to the pin 116 in the C-direction in FIG. 5 are defined as the same distance to each other. Namely, the driven arm 214 and the spindle connecting arm 215 are connected in a relatively rotatable manner to each other on a line on which the bearing 213 is moved in the A-direction. Therefore, the moment is not exerted on the bearing 213 by the driven arm 214. Accordingly, unlike the first embodiment, only one bearing 213 is provided in the second embodiment. As a result, a number of the bearing is reduced.

In the second embodiment described above, the connecting part of the driven arm 214 and the spindle connecting arm 215 is parallelly arranged with the eccentric moving portion 104 in the C-direction, however it is not limited to such construction. For example, the connecting part of the driven arm 214 and the spindle connecting arm 215 may be arranged at an overlapped area with the eccentric moving portion 104 as viewed in a longitudinal direction of the spindle 120. According to such construction, a distance from the spindle 120 to the eccentric moving portion 104 and a distance from the spindle 120 to the pin 116 are defined as the same distance in the C-direction.

In the first and the second embodiment, the groove 116a is spirally formed on the outer surface of the pin 116, however the groove is not limited to such spiral groove. For example, the groove 116a may be extended in a line or a curved line. Further, a recess such as a hole or a groove for holding a lubricant may be provided on an inner surface of the through-holes of the driven arm 114, 214 and/or the spindle connecting arm 115, 215.

Further, in the first embodiment and the second embodiment, the driven arm 114, 214 and the spindle connecting arm 115, 215 are connected via the pin 116, however it is not limited to such construction. For example, one of the components during the driven arm 114, 214 and the spindle connecting arm 115, 215 may be provided integrally with a pin, and further a through-hole may be provided on the other component. According to such construction, the pin is not necessary to provide separately, therefore a number of the components of the electric oscillating tool 100 is reduced.

Further, in the first embodiment and the second embodiment, the blade 200 is attached to the spindle 120, however it is not limited to such construction. For example, an attached shaft to which the blade 200 is attached, which is other than the spindle 120, may be provided. In this construction, the attached shaft may be preferred to be arranged coaxially to the spindle 120. On the other hand, the attached shaft may be parallelly arranged and offset to the spindle 120. In case that the attached shaft is offset to the spindle 120, a transmitting member which transmits a rotation of the spindle 120 to the attached shaft may be provided.

Having regard to an aspect of the invention, following features are provided:

(Feature 1)

A power tool according to claim 5, wherein the pivot portion includes a cylindrical member which is parallelly arranged to the driving shaft, and wherein the lubricant holding portion is defined as a spiral groove which is formed on an outer surface of the cylindrical member.

DESCRIPTION OF NUMERALS

100 electric oscillating tool
101 main housing
102 driving mechanism
103 tool holding mechanism
104 eccentric moving portion
110 motor
111 output shaft
112 eccentric shaft
113a first bearing
113b second bearing
114 driven arm
114a first arm
114b second arm
115 spindle connecting arm
116 pin
116a groove
117 C-ring
118 pivot
120 spindle
121 inner flange
122 outer flange
123 bearing
200 blade
213 bearing
214 driven arm
214a first arm
214b second arm
215 spindle connecting arm

What is claimed is:

1. A power tool which actuates a tool around a predetermined axis, comprising: a motor; a driving shaft which is driven by the motor; and a driving transmission member which transmits a rotation output of the motor to the driving shaft, wherein the driving transmission member includes (i) an eccentric moving member which moves eccentrically around a rotational shaft of the motor, (ii) a first member to which a movement of the eccentric moving member is transmitted, (iii) a second member which is a different and separate member from the first member, one side of the second member being fixed to the driving shaft and the second member rotating together with the driving shaft around an axial direction of the driving shaft, and (iv) a pivot portion which connects the first member and another side of the second member such that the second member rotates around the axial direction of the driving shaft when the first member is moved by the movement of the eccentric moving member, wherein the eccentric moving member includes an eccentric portion which is arranged to be offset to the center of the rotational shaft, and two bearings which are arranged on a periphery of the eccentric portion, wherein the first member includes two arms which face each other, each of the two arms contacts with respective peripheries of the two bearings simultaneously, and wherein the two bearings are arranged in line in the axial direction of the rotational shaft.

2. The power tool according to claim 1, wherein the pivot portion and the eccentric moving member are arranged to be equally distant from the driving shaft in the axial direction of the rotational shaft.

3. The power tool according to claim 1, wherein a tool attached shaft to which the tool is attached is arranged coaxially to the driving shaft.

4. The power tool according to claim 1, wherein the pivot portion includes a lubricant holding portion which holds lubricant for lubricating the first member and the second member during rotation.

5. The power tool according to claim 1, wherein the pivot portion includes an elongate member which is arranged parallel to the driving shaft.

* * * * *